(12) United States Patent
Kim et al.

(10) Patent No.: US 9,702,854 B2
(45) Date of Patent: Jul. 11, 2017

(54) PHOTOACOUSTICBRACKET, PHOTOACOUSTIC PROBE AND PHOTOACOUSTIC IMAGING APPARATUS HAVING THE SAME

(71) Applicant: SAMSUNG MEDISON CO., LTD., Gangwon-Do (KR)

(72) Inventors: Jung Ho Kim, Seoul (KR); Jung Taek Oh, Seoul (KR)

(73) Assignee: Samsung Medison Co., Ltd., Hongcheon-gun, Gangwon-do (KR)

( * ) Notice: Subject to any disclaimer, the term of this patent is extended or adjusted under 35 U.S.C. 154(b) by 88 days.

(21) Appl. No.: 14/279,108

(22) Filed: May 15, 2014

(65) Prior Publication Data

US 2014/0340685 A1    Nov. 20, 2014

(30) Foreign Application Priority Data

May 20, 2013    (KR) .......................... 10-2013-0056659

(51) Int. Cl.
| | |
|---|---|
| G01N 29/24 | (2006.01) |
| A61B 5/00 | (2006.01) |
| A61B 17/34 | (2006.01) |
| A61B 10/02 | (2006.01) |
| A61B 8/00 | (2006.01) |

(52) U.S. Cl.
CPC ....... G01N 29/2418 (2013.01); A61B 5/0095 (2013.01); A61B 8/4209 (2013.01); A61B 8/4281 (2013.01); A61B 10/0233 (2013.01); A61B 17/3403 (2013.01); A61B 2017/3413 (2013.01); A61B 2562/247 (2013.01)

(58) Field of Classification Search
CPC ............ A61B 10/0233; A61B 17/3403; A61B 2017/3413; A61B 2562/247; A61B 5/0095

See application file for complete search history.

(56) References Cited

U.S. PATENT DOCUMENTS

| 4,158,773 A * | 6/1979 | Novak ................... G01T 1/202 250/361 R |
| 4,630,607 A * | 12/1986 | Duinker ............. A61B 17/2251 601/4 |
| 6,305,083 B1 * | 10/2001 | Rijken .................. A61C 17/22 156/274.4 |

(Continued)

FOREIGN PATENT DOCUMENTS

| EP | 2 548 516 A1 | 1/2013 |
| JP | 2008-049063 A | 3/2008 |

OTHER PUBLICATIONS

European Office Action issued in European Application No. 14158077.9-1660 dated Aug. 14, 2014.

(Continued)

*Primary Examiner* — Baisakhi Roy
(74) *Attorney, Agent, or Firm* — McDermott Will & Emery LLP

(57) ABSTRACT

In accordance with one exemplary embodiment of the present invention, a photoacoustic probe includes: at least one optical fiber irradiating laser to a target; an ultrasonic probe collecting a photoacoustic signal generated by the target having absorbed the laser; and a fluid-type light reflector reflecting laser reflected, scattered, or deflected from the target.

20 Claims, 21 Drawing Sheets

(56) References Cited

U.S. PATENT DOCUMENTS

| | | | |
|---|---|---|---|
| 2009/0158821 A1* | 6/2009 | Sun | G01N 15/06 73/61.75 |
| 2009/0326617 A1* | 12/2009 | Asano | A61B 5/02007 607/89 |
| 2010/0053618 A1 | 3/2010 | Nakajima et al. | |
| 2010/0094134 A1 | 4/2010 | Zhu et al. | |
| 2010/0277721 A1* | 11/2010 | Kolodner | G02B 26/004 356/213 |
| 2012/0179022 A1 | 7/2012 | Ichihara et al. | |
| 2012/0253200 A1* | 10/2012 | Stolka | A61B 1/041 600/459 |
| 2013/0064771 A1 | 3/2013 | Wada | |
| 2013/0218024 A1* | 8/2013 | Boctor | A61B 8/4254 600/476 |
| 2014/0073899 A1* | 3/2014 | Cohrs | A61B 5/6833 600/407 |
| 2014/0076055 A1* | 3/2014 | Asao | G01H 9/00 73/655 |
| 2014/0345385 A1* | 11/2014 | Irisawa | A61B 5/0095 73/609 |

OTHER PUBLICATIONS

European Office Action issued in Application No. 14 158 077.9 dated Jun. 22, 2016.

Communication and European Search Report EP Application No. 14 15 8077 dated Mar. 6, 2015.

Chulhong Kim et al., "Handheld array-based photoacoustic probe for guiding needle biopsy of sentinal lymph nodes", Journal of Biomedical Optics 15(4), 046010 (Jul./Aug. 2010), pp. 046010-1-046010-4.

Roy G.M. Kolkman et al., "Real-time in vivo photoacoustic and ultrasound imaging", Journal of Biomedical Optics, Sep./Oct. 2008, vol. 13(5), pp. 050510-1-050510-3.

European Intention to Grant issued in Application No. 14158077.9 dated Mar. 16, 2017.

* cited by examiner

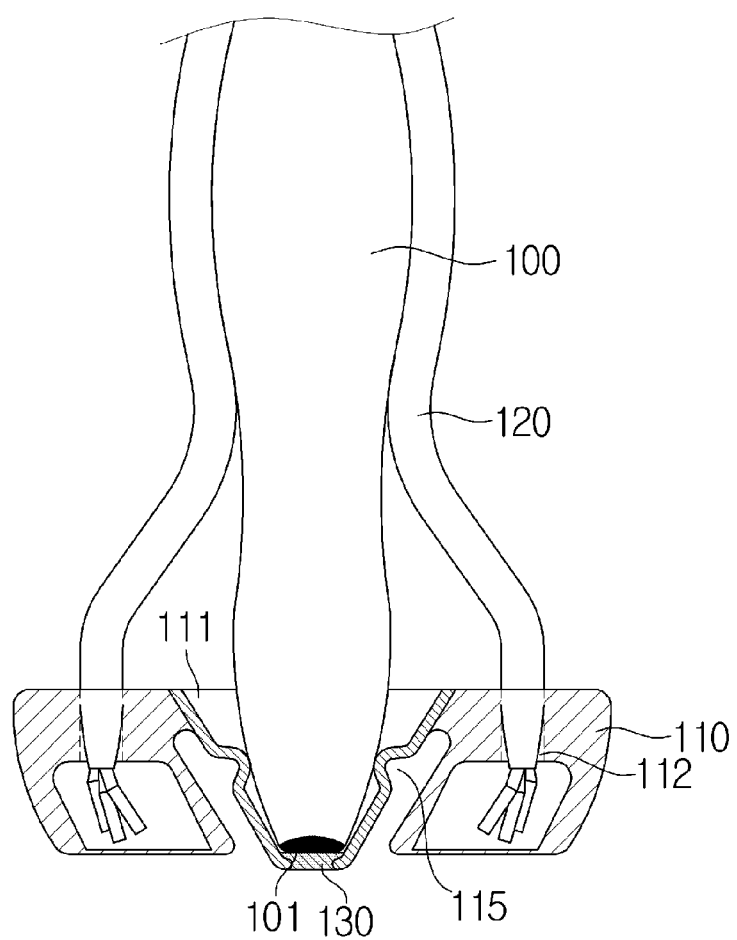

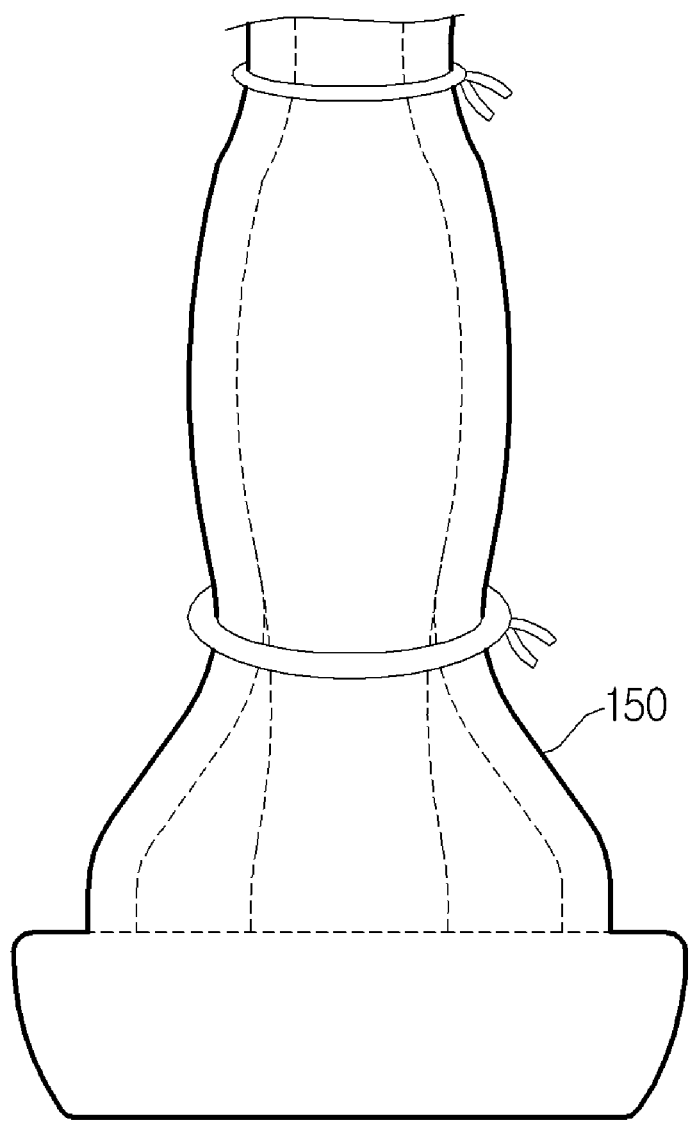

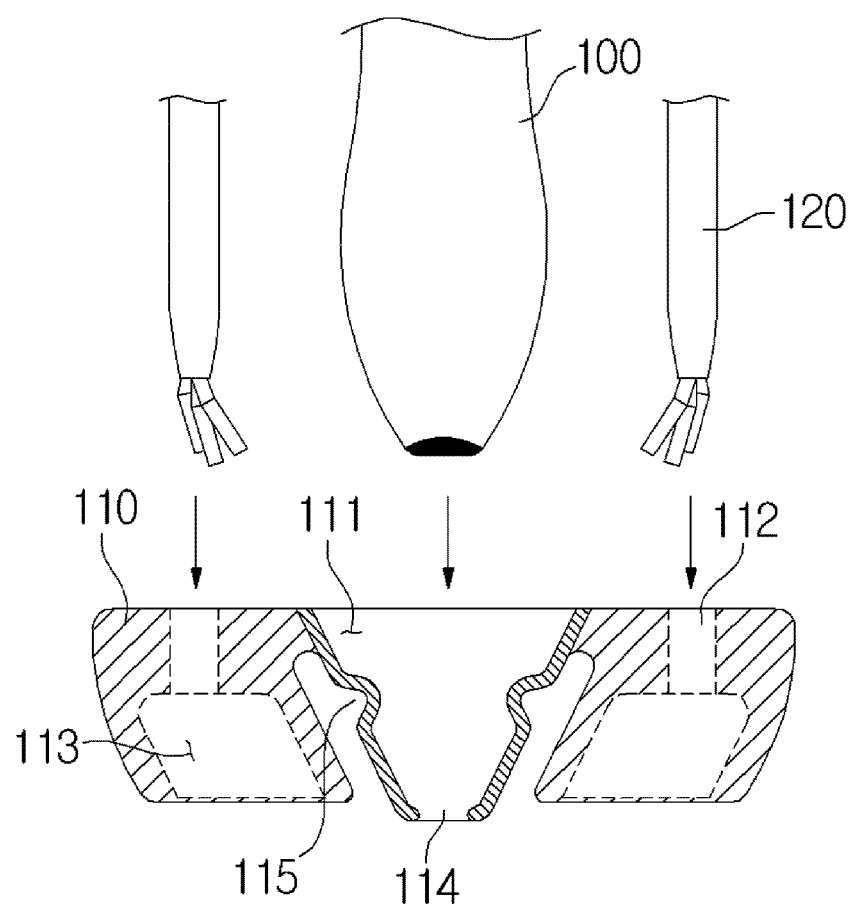

PHOTOACOUSTICBRACKET, PHOTOACOUSTIC PROBE AND PHOTOACOUSTIC IMAGING APPARATUS HAVING THE SAME

CROSS-REFERENCE TO RELATED APPLICATION

This application claims the benefit of Korean Patent Application No. 2013-0056659, filed on May 20, 2013, in the Korean Intellectual Property Office, the disclosure of which is incorporated herein by reference.

BACKGROUND

1. Field

Embodiments of the present invention relate to a structure of a photoacoustic probe for receiving photoacoustic waves generated from a material that has absorbed light, and a photoacoustic imaging apparatus having the photoacoustic probe.

2. Description of the Related Art

In general, medical imaging apparatuses irradiate ultrasonic waves, laser, X-rays, or the like to a target, acquire an image of the target according to transmission, absorption, and reflection properties of the target, and use the acquired image of the target for diagnosis. The medical imaging apparatuses include an ultrasonic imaging apparatus, a photoacoustic imaging apparatus, an X-ray imaging apparatus, etc.

A photoacoustic imaging technique noninvasively images the inner tissue of a target using a photoacoustic effect, wherein the photoacoustic effect is an effect in which a certain material generates acoustic waves when absorbing light or electromagnetic waves.

In order to obtain photoacoustic images, a light source for irradiating light to a target and a probe for receiving photoacoustic waves generated from the inside material of the target are used. However, when irradiated light is scattered by certain scattering materials in a target and then received by the probe, artifacts are made in the resultant photoacoustic image.

SUMMARY

In accordance with one aspect of the present invention, a photoacoustic probe includes: at least one optical fiber irradiating laser to a target; an ultrasonic probe collecting a photoacoustic signal generated by the target having absorbed the laser; and a fluid-type light reflector reflecting laser reflected, scattered, or deflected from the target.

A laser generator may be connected to one end of the optical fiber.

When a plurality of optical fibers are provided, the plurality of optical fibers may be connected in series or in parallel to the laser generator.

The laser may be single-wavelength laser or multi-wavelength laser.

The laser may be pulsed laser or continuous laser.

The ultrasonic probe may be a linear probe, a convex probe, or a phased array probe.

The fluid-type light reflector may be a fluid containing zinc oxide (ZnO) or titanium oxide (TiO).

The photoacoustic probe may further include a photoacoustic bracket with which the ultrasonic probe and the optical fiber are coupled.

The photoacoustic bracket may include a space in which the light reflector is placed.

The photoacoustic probe may include an inner cover blocking the light reflector from leaking out.

The photoacoustic probe may include an outer cover covering the outer surface of the photoacoustic probe in order to avoid cross-contamination of the target.

The inner cover and the outer cover may be made of a rubber material that transmits both ultrasonic waves and laser.

The inner cover and the outer cover may be connected to each other by a Radio Frequency (RF) adhesion process.

The photoacoustic bracket may be coupled with a biopsy needle kit.

The target may include a biologic tissue and a non-biologic tissue.

In accordance with another aspect of the present invention, a photoacoustic imaging apparatus includes: a photoacoustic probe irradiating laser to a target and collecting a photoacoustic signal; and a main body converting the collected photoacoustic signal into an image signal, wherein the photoacoustic probe comprises a fluid-type light reflector reflecting laser reflected, scattered, or deflected from the target.

The photoacoustic probe may include a photoacoustic bracket with which the optical fiber is coupled.

The photoacoustic bracket may include a space in which the light reflector is placed.

The photoacoustic probe may include an inner cover blocking the light reflector placed in the photoacoustic bracket from leaking out.

The photoacoustic probe may include an outer cover covering the outer surface of the photoacoustic probe in order to avoid cross-contamination of the target.

In accordance with another aspect of the present invention, a photoacoustic bracket includes: a probe coupling part with which an ultrasonic probe is coupled; an optical fiber coupling part with which an optical fiber is coupled; and a space in which a light reflector is placed.

The optical fiber coupling part may include: an optical fiber inserting hole in which the optical fiber is inserted; and an inner space in which an end of the optical fiber is placed.

The photoacoustic bracket may include a groove holding an inner cover for blocking the light reflector from leaking out.

The photoacoustic bracket may include a biopsy needle kit coupler that is coupled with a photoacoustic biopsy needle kit.

BRIEF DESCRIPTION OF THE DRAWINGS

These and/or other aspects of the invention will become apparent and more readily appreciated from the following description of the embodiments, taken in conjunction with the accompanying drawings of which:

FIGS. 5A, 5B, and 5C illustrate a photoacoustic probe according to an exemplary embodiment of the present invention when optical fibers and an ultrasonic probe are coupled with the photoacoustic bracket;

FIGS. 7A, 7B, and 7C illustrate a photoacoustic probe including a photoacoustic bracket covered with an inner cover and an outer cover, according to an exemplary embodiment of the present invention;

FIGS. 9A, 9B, and 9C illustrate an order in which a conventional ultrasonic probe is used as a photoacoustic probe.

DETAILED DESCRIPTION

Figure 1:
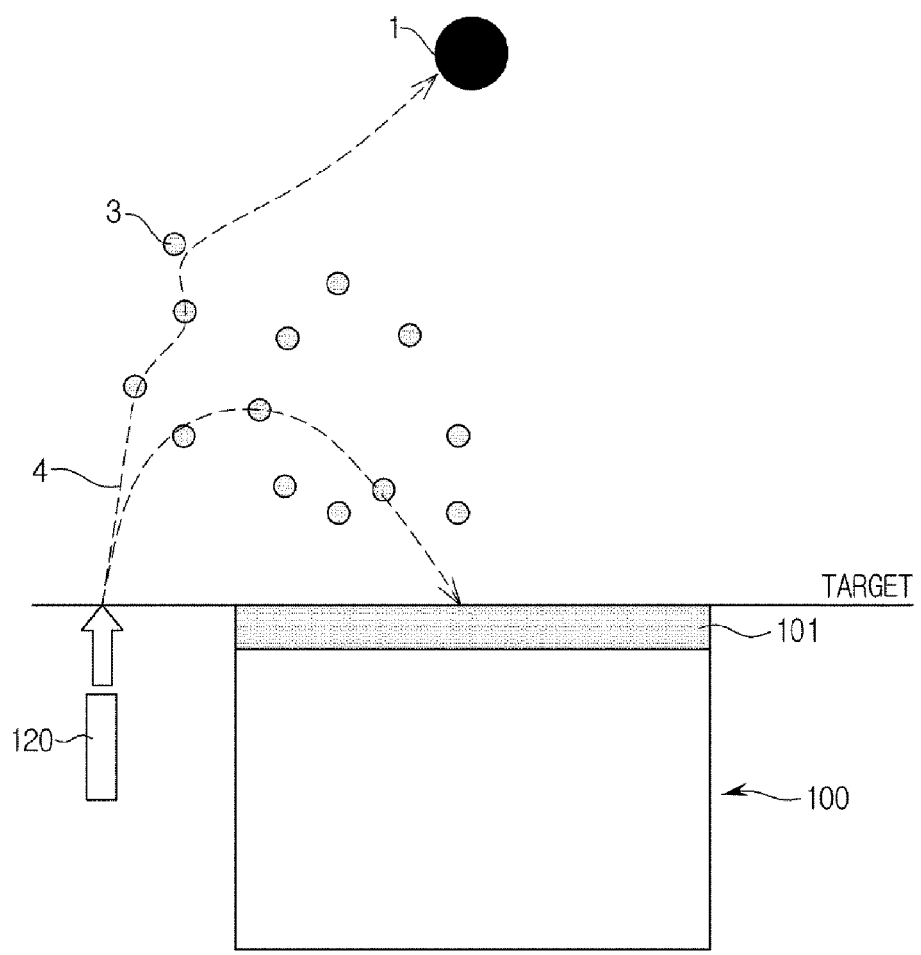
FIG. 1 is a view for describing a problem that might be generated when a photoacoustic probe irradiates light to a target.

Reference will now be made in detail to the embodiments of the present invention, examples of which are illustrated in the accompanying drawings, wherein like reference numerals refer to like elements throughout.

As a medical imaging technology for diagnosing a target, a photoacoustic imaging (PAI) technology has been developed which diagnoses a target by combining the ultrasonic characteristics of the target with the photoacoustic characteristics of the target.

The PAI technology, which combines high spatial resolution of ultrasonic images with a high contrast ratio of optical images, is suitable to image biologic tissues. More specifically, when laser having a short pulse duration in a unit of nanoseconds is irradiated to biologic tissues, the short electromagnetic pulses of the laser are absorbed in the biologic tissues, and momentary acoustic waves are generated by thermo-elastic expansion in a tissue region acting as a source of initial acoustic waves, wherein most of the acoustic waves is ultrasonic waves. The ultrasonic waves arrive at the biologic tissues where signals are acquired at different times, and the ultrasonic waves are finally displayed as a photoacoustic image. In the following exemplary embodiments, the term "photoacoustic waves" mean acoustic waves generated by absorption of light.

An ultrasonic imaging technology is a well-known and widely used technology to diagnose lesions in a human body using ultrasonic waves. Ultrasonic images are created by irradiating ultrasonic waves to a target and then receiving and imaging ultrasonic waves reflected from the inside materials of the target. The ultrasonic images include a B-mode image to represent a section of a target, an elastic image to represent elasticity information of a target, an M-mode image to represent biological information about a specific region of a target, and a color Doppler image to visualize blood flow in real time.

Photoacoustic images can be combined with ultrasonic images. For example, by irradiating ultrasonic waves to a specific region of a target to obtain an ultrasonic image, then irradiating laser to the same specific region of the target to obtain a photoacoustic image, and comparing and analyzing the two images, an absorption rate of the specific region as well as an anatomical structure of the specific region can be recognized.

FIG. 1 is a view for describing a problem that might be generated when a photoacoustic probe irradiates light to a target.

A photoacoustic probe is an apparatus to receive photoacoustic waves or photoacoustic signals from the inside of a target and convert them into electrical signals. In the following description, the term "photoacoustic waves" mean photoacoustic signals. The electrical signals are transferred to a main body and used to create photoacoustic images.

The photoacoustic probe may be configured to acquire only photoacoustic images or both ultrasonic images and photoacoustic images. In the latter case, the photoacoustic probe has a structure capable of transmitting ultrasonic waves as well as receiving ultrasonic waves. The photoacoustic probe may be implemented as a general ultrasonic probe for transmitting and receiving ultrasonic signals, or may be combined with optical fibers for irradiating light so that irradiation of light and reception of ultrasonic waves can be performed by a single apparatus. In the following description, a photoacoustic probe in which an ultrasonic probe is combined with an optical fiber is assumed.

Referring to FIG. 1, a photoacoustic probe includes a target contact part 101 contacting a target in one end. The target contact part 101 may be an acoustic lens for focusing ultrasonic waves.

The target may contain a plurality of light scatterers 3 that scatter light. When laser 4 having a specific wavelength is irradiated to the target, the laser 4 penetrates the target, so that a part of the laser 4 arrives at a target material 1 which is a light absorber to generate acoustic waves, and the other part of the laser 4 is scattered by the light scatterers 3 and then incident to the target contact part 101. When the target contact part 101 has been made of a material absorbing laser, the target contact part 101 also generates acoustic waves by absorbing the laser 4, and the generated acoustic waves are again radiated thus make artifacts in a resultant photoacoustic image.

In the following description, for convenience of description, acoustic waves generated by light absorption are assumed to be photoacoustic waves, and the target contact unit 101 of the photoacoustic probe is assumed to be an acoustic lens.

Figure 2:
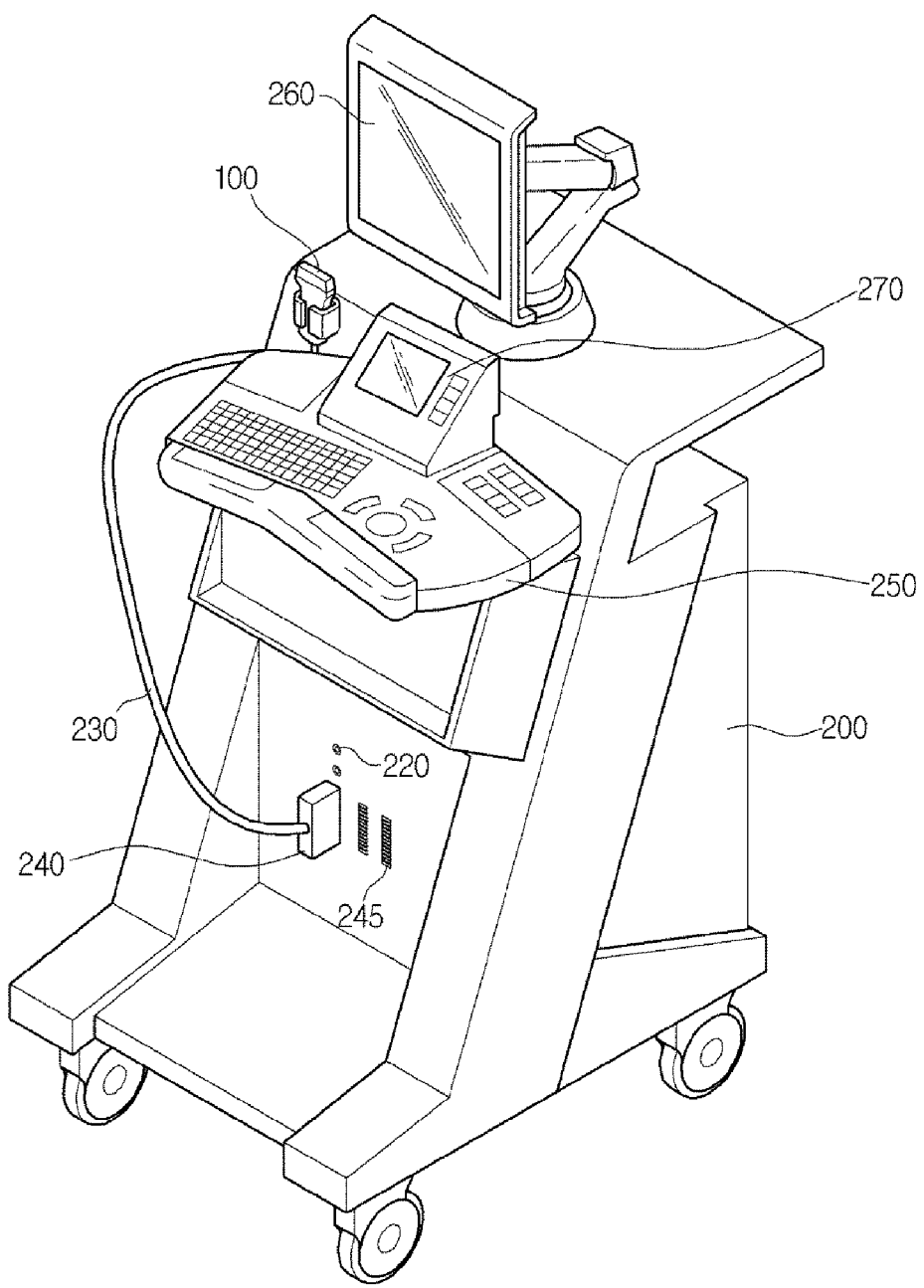
FIG. 2 is a perspective view of a photoacoustic imaging apparatus having a built-in laser generator, according to an exemplary embodiment of the present invention.

FIG. 2 is a perspective view of a photoacoustic imaging apparatus having a built-in laser generator, according to an exemplary embodiment of the present invention. Referring to FIG. 2, the photoacoustic imaging apparatus may include a main body 200, a photoacoustic probe, an input unit 250, a main display 260, and a sub display 270. The photoacoustic probe may include an ultrasonic probe 100.

In the main body 200, a controller for receiving photoacoustic signals collected by the ultrasonic probe 100 and converting the photoacoustic signals into photoacoustic images may be installed. A photoacoustic image has an advantage that it can show a functional image of tissues, based on a fact that tissues having different functional factors have different absorption rates with respect to a specific wavelength of laser although they have the same anatomical structure and accordingly cannot be distinguished by ultrasonic waves.

One or more female connectors 245 are provided in one side of the main body 200. A male connector 240 connected to a cable 230 may be physically coupled with one of the female connectors 245.

Also, one or more optical fiber coupling terminals 220 with which one ends of optical fibers 120 (see FIG. 1) can be coupled may be provided. The optical fiber coupling terminals 220 may be connected to a laser generator installed inside or outside the photoacoustic imaging apparatus so that laser generated by the laser generator can be transferred to the photoacoustic probe along the optical fibers 120. The optical fibers 120 may be connected in series or in parallel to the laser generator through the optical fiber coupling terminals 220. That is, the photoacoustic probe may connect to the laser generator in an arbitrary manner.

The input unit 250 allows a user to input commands for operating the photoacoustic imaging apparatus. For example, a user may input a command for starting photoacoustic diagnosis through the input unit 250, or may set a wavelength of light through the input unit 250. Commands input through the input unit 250 may be transmitted to the main body 200 through wired/wireless communication.

The input unit 250 may include at least one of a keyboard, a foot switch, and a foot pedal. The keyboard may be hardwarily implemented and mounted on the upper part of the main body 200. The keyboard may include at least one of switches, keys, a joystick, and a trackball. As another example, the keyboard may be softwarily implemented like a Graphic User Interface (GUI). In this case, the keyboard may be displayed on the screen of the main display 260 or the sub display 270. The foot switch or the foot pedal may be provided in the lower part of the main body 200, and the user may control operations of the photoacoustic imaging apparatus using the foot pedal.

The sub display 270 may be mounted on the main body 200. In the example of FIG. 2, the sub display 270 is provided in the upper part of the input unit 250. The sub display 270 may display an application associated with operations of the photoacoustic imaging apparatus. For example, the sub display 270 may display a menu, guide information, and the like for photoacoustic diagnosis. The sub display 270 may be implemented as a Cathode Ray Tube (CRT), a Liquid Crystal Display (LCD), etc.

The main display 260 may be provided in the main body 200. In the example of FIG. 2, the main display 260 is positioned above the sub display 270. The main display 260 may display photoacoustic images acquired during photoacoustic diagnosis. The main display 260 may be, like the sub display 270, implemented as a CRT or a LCD. FIG. 2 shows a case in which the main display 260 is coupled with the main body 200, however, it is also possible that the main display 260 is detachably attached to the main body 200.

In the example of FIG. 2, the photoacoustic imaging apparatus includes both the main display 260 and the sub display 270. However, in some cases, the sub display 270 may be omitted. In this case, the main display 260 may display applications, menus, etc., instead of the sub display 270.

Figure 3:
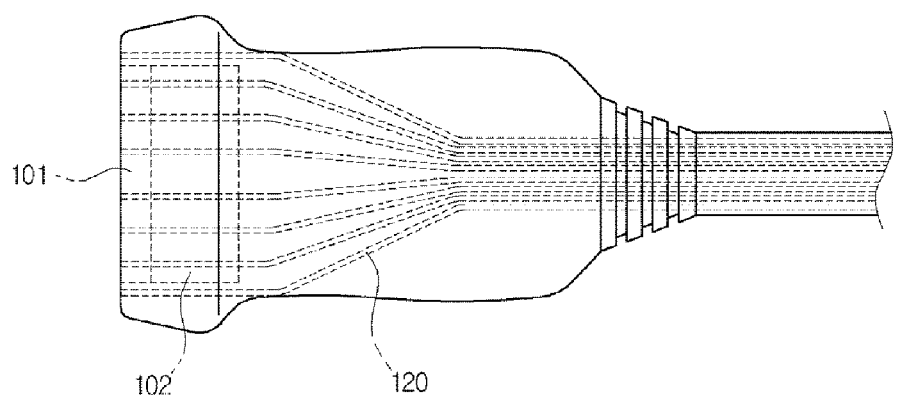
FIG. 3 is a top view of a photoacoustic probe in which an ultrasonic probe is combined with optical fibers.

FIG. 3 is a top view of a photoacoustic probe in which an ultrasonic probe is combined with optical fibers. Referring to FIG. 3, a ultrasonic probe 100 includes a piezoelectric module 102 to transmit and receive ultrasonic waves, an acoustic lens 101 disposed in front of the piezoelectric module 102 to focus ultrasonic waves, and optical fibers 120 to irradiate laser of a specific wavelength to a target. A laser generator for generating laser may be installed in a photoacoustic imaging apparatus, and a wavelength of laser that is to be generated by the laser generator may be appropriately selected in consideration of inside materials of a target.

The photoacoustic imaging apparatus is an apparatus for imaging the inner tissue of a target using a photoacoustic effect, and since the photoacoustic imaging apparatus includes the ultrasonic probe 100 capable of transmitting and receiving ultrasonic waves, the photoacoustic imaging apparatus can also create a ultrasonic image of a target.

The piezoelectric module 102 includes a piezoelectric layer for converting electrical signals into acoustic signals and vice versa, a matching layer disposed in front of the piezoelectric layer, and a backing layer disposed behind the piezoelectric layer.

A phenomenon in which a voltage is generated when a mechanical pressure is applied to a specific material is called a piezoelectric effect, and a phenomenon in which mechanical deformation occurs when a voltage is applied to a specific material is called a converse piezoelectric effect. Materials having the piezoelectric effect and converse piezoelectric effect are piezoelectric materials. That is, piezoelectric materials are materials capable of converting electricity energy into mechanical vibration energy and vice versa.

The piezoelectric layer, which is made of a piezoelectric material, receives electrical signals, and converts the electrical signals into mechanical vibration to generate ultrasonic waves, and if receiving ultrasonic signals, the piezoelectric layer converts the ultrasonic signals into electrical signals.

The piezoelectric material forming the piezoelectric layer may include ceramic of lead zirconate titanate (PZT), PMN-PT single crystals consisting of a solid solution of lead magnesium niobate (PMN) and lead titanate (PT), and PZN-PT single crystals consisting of a solid solution of lead zinc niobate (PZN) and lead titanate (PT).

The matching layer is disposed in front of the piezoelectric layer, and reduces a difference in acoustic impedance between the piezoelectric layer and a target so that ultrasonic waves generated by the piezoelectric layer can be effectively transferred to the target. The matching layer may be comprised of one or more layers, and may be divided into a plurality of units each having a predetermined width, together with the piezoelectric layer, by a dicing process.

The backing layer is disposed behind the piezoelectric layer, and absorbs ultrasonic waves generated by the piezoelectric layer to block the ultrasonic waves from being transferred behind the piezoelectric layer, thereby preventing image distortion. The backing layer may be comprised of a plurality of layers in order to improve an attenuation/blocking effect with respect to ultrasonic waves.

The acoustic lens 101 is disposed in front of the piezoelectric module 102, specifically, in front of the matching layer, to focus ultrasonic waves that are to be transmitted or received ultrasonic waves.

The optical fibers 120 irradiate laser of a specific wavelength generated by the laser generator to a target. An alignment of the optical fibers 120 will be described later.

The laser generator may generate single-wavelength laser or multi-wavelength laser. Also, the laser generator may generate pulsed laser or continuous laser. That is, the laser generator may generate various kinds or properties of laser. Accordingly, the laser generator may be a light-emitting device capable of generating a specific wavelength component or single-color light having such a specific wavelength component, such as a Laser Diode (LD), a Light-Emitting Diode (LED), a solid-state laser, and a gas laser.

For example, when the photoacoustic probe measures a hemoglobin concentration of a target, a Nd:YAG laser (a solid-state laser) capable of generating laser having a wavelength of about 1,000 nm or a He—Ne gas laser capable of generating laser having a wavelength of 633 nm is used to generate a laser beam having a pulse width of about 10 nsec. Generally, hemoglobin absorbs light ranging from 600 nm to 1,000 nm although the hemoglobin has different optical absorption properties according to its type. An emission wavelength ranging from 550 nm to 650 nm can be generated using a small light-emitting device, such as a LD or a LED, made of InGaAlP, an emission wavelength ranging from 650 nm to 900 nm can be generated using a small light-emitting device (a LD or a LED) made of GaAlAs, and an emission wavelength ranging from 900 nm to 2,300 nm can be generated using a small light-emitting device (a LD or a LED) made of InGaAs or InGaAsP. Also, an Optical Parametrical Oscillators (OPO) laser capable of changing a wavelength using nonlinear photonic crystals may be used.

In order to overcome the problem of artifacts that are generated by the photoacoustic probe having the above-described structure, a photoacoustic probe having an improved structure has been proposed. Hereinafter, the photoacoustic probe having the improved structure will be described in detail.

Figure 4A:
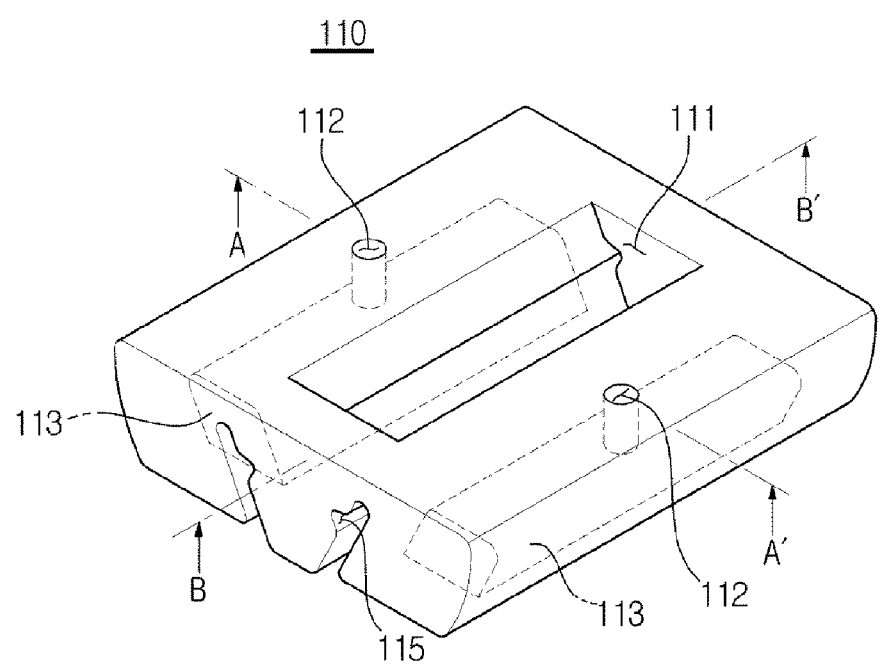
FIGS. 4A, 4B, and 4C illustrate a photoacoustic bracket according to an exemplary embodiment of the present invention.
Figure 4B:
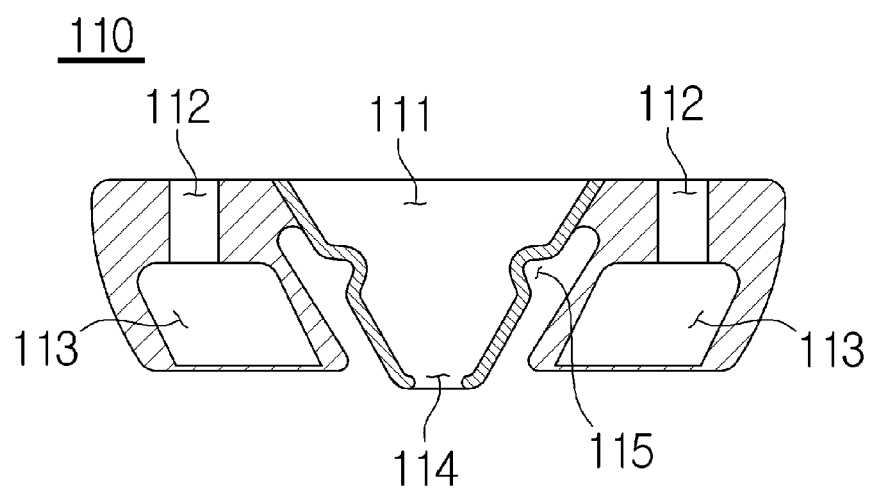
Figure 4C:
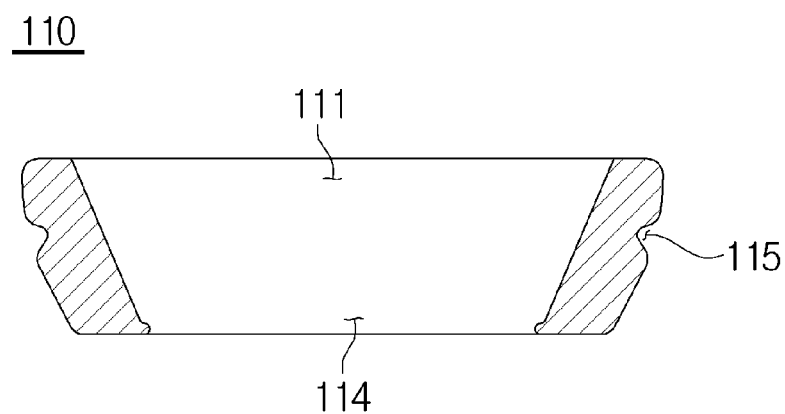

FIGS. 4A, 4B, and 4C illustrate a photoacoustic bracket according to an exemplary embodiment of the present invention, wherein FIG. 4A is a perspective view of the photoacoustic bracket, FIG. 4B is a front sectional view of the photoacoustic bracket, and FIG. 4C is a side sectional view of the photoacoustic bracket. Here, the front sectional view of the photoacoustic bracket is a sectional view appearing when the photoacoustic bracket illustrated in FIG. 4A is cut along a line A-A', and the side sectional view of the photoacoustic bracket is a sectional view appearing when the photoacoustic bracket illustrated in FIG. 4A is cut along a line B-B'.

Referring to FIGS. 4A, 4B, and 4C, the photoacoustic bracket has three grooves. When shown from the top, a groove located in the center of the photoacoustic bracket is a probe coupling part 111 with which an ultrasonic probe 100 is coupled. The probe coupling part 111 may be formed in a specific shape corresponding to the ultrasonic probe 100 such that the ultrasonic probe 100 can be stably inserted in the probe coupling part 111. The external appearance of the photoacoustic bracket 110 may be formed in a specific shape such that the ultrasonic probe 100 can be stably fixed in the photoacoustic bracket 110 using a method such as interference fit or notch.

Optical fiber coupling parts may be formed to be opposite to each other with the probe coupling part 111 in between. Each of the optical fiber coupling parts may include an optical fiber inserting hole 112 through which optical fibers are inserted and an inner space 113 in which one ends of the optical fibers are placed. When shown from the top, the optical fiber inserting hole 112 may be in the shape of a circle. Below the optical inserting hole 112, the inner space 113 in which one ends of optical fibers are placed is formed with a wide area so that the optical fibers can be uniformly distributed over the wide area. The inner space 113 in which the ends of the optical fibers are placed helps laser output from the optical fibers arrive at a target without any interference. In FIGS. 4A, 4B, and 4C, two optical fiber inserting holes 112 are provided, however, the number of optical fiber inserting holes is not limited so long as the photoacoustic bracket 110 includes one or more optical fiber inserting hole.

When the ultrasonic probe 100 is inserted in the photoacoustic bracket 110, a space may be formed below the acoustic lens 101 of the ultrasonic probe 100. The space is a space 114 in which a fluid-type light reflector 130 is to be placed. The depth of the space 114 decides the thickness of the light reflector 130 that is to beplaced.

The light reflector 130 placed in the space 114 is fluid, and accordingly, the light reflector 130 may overflow or permeate through gaps of the photoacoustic bracket 110 to interfere with transmission path of laser output from the optical fibers. Accordingly, in order to prevent the light reflector 130 from leaking into the inner spaces 113 in which the ends of the optical fibers are placed, a groove 115 for securely holding an inner cover may be formed.

Figure 5A:
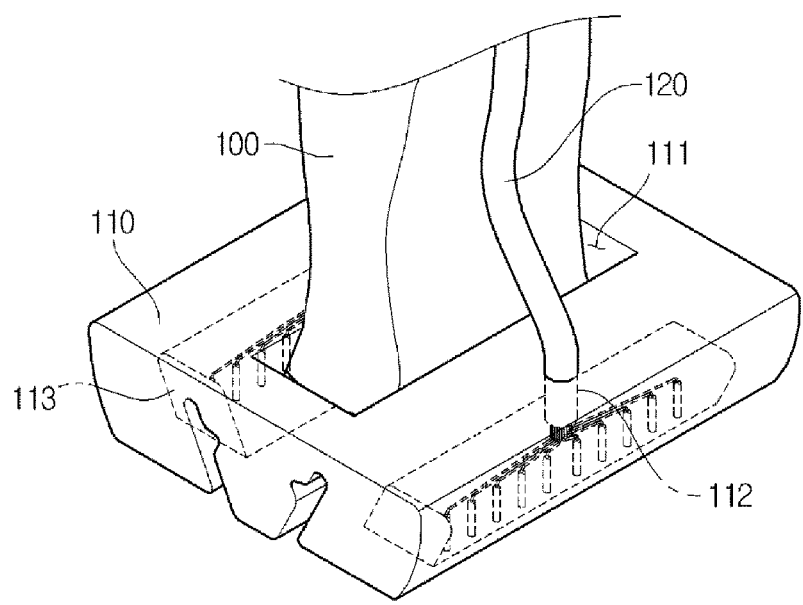
Figure 5C:
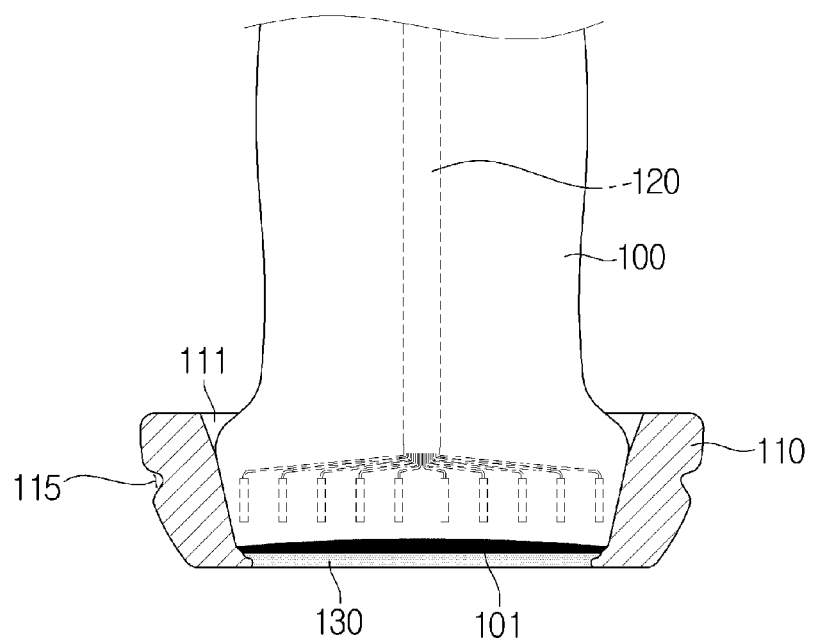

FIGS. 5A, 5B, and 5C illustrate the photoacoustic probe according to an exemplary embodiment of the present invention when the optical fibers 120 and the ultrasonic probe 100 are coupled with the photoacoustic bracket 110, wherein FIG. 5A is a perspective view of the photoacoustic probe, FIG. 5B is a front sectional view of the photoacoustic probe, and FIG. 5C is a side sectional view of the photoacoustic probe.

Referring to FIGS. 5A, 5B, and 5C, the ultrasonic probe 100 may be coupled with the probe coupling part 111 of the photoacoustic bracket 110. As described above, the ultrasonic probe 100 may be coupled with the photoacoustic bracket 110 using a method such as interference fit or notch.

The ultrasonic probe 100 that is coupled with the photoacoustic bracket 110 may be a linear probe, a convex probe, or a phased array probe. That is, the kind of the ultrasonic probe 100 is not limited. The shape of the photoacoustic bracket 110 may depend on the kind of the ultrasonic probe 100 such that the ultrasonic probe 100 can be easily coupled with the photoacoustic bracket 110.

Optical fibers may be inserted into optical fiber inserting holes 112. In FIGS. 5A, 5B, and 5C, the optical fibers are provided as a plurality of bundles of optical fibers, and accordingly, the optical fibers may be uniformly distributed in the inner spaces 113 in which the ends of the optical fibers are placed.

A fluid-type light reflector 130 may be placed in the space 114 formed below the acoustic lens 101 of the ultrasonic probe 100. The light reflector 130 reflects laser scattered from a target and then directed toward the acoustic lens 101 to redirect the laser toward the target, thereby minimizing generation of artifacts.

The light reflector 130 may be a material having photo-reflectance. For example, the light reflector 130 may contain zinc oxide (ZnO) or titanium oxide (TiO) which is main ingredients of sunblock. However, ultrasonic waves have not to be blocked by the light reflector 130 since the ultrasonic waves should be collected by the acoustic lens 101 in order to acquire accurate photoacoustic images. Accordingly, the light reflector 130 may be a material capable of minimizing or reducing scattering of ultrasonic waves while reflecting light.

The light reflector 130 may be fluid. A solid-type light reflector requires a separate layer for impedance matching between the light reflector and an acoustic lens. However, a fluid-type light reflector requires no separate layer for impedance matching. The reason is because the light reflector itself acts as couplant for ultrasonic waves. Accordingly, photoacoustic ultrasonic waves can be generated without using any separate component in addition to attaching the ultrasonic probe 100 and the optical fibers 120 to the photoacoustic bracket 110.

Since the light reflector 130 is fluid, as described above, the light reflector 130 may overflow to enter the inner spaces 113 in which the ends of the optical fibers are placed. Also, the light reflector 120 may permeate through gaps of the photoacoustic bracket 110 to interfere with the transmission path of laser irradiated from the optical fibers 120.

In order to overcome the problem, the photoacoustic bracket 110 may include a groove 115 for holding an inner cover so as to prevent the light reflector 130 from leaking out. A method for holding an inner cover such that it is securely attached to the photoacoustic bracket 110 through the groove 115 will be described with reference to FIG. 6, below.

Figure 6A:
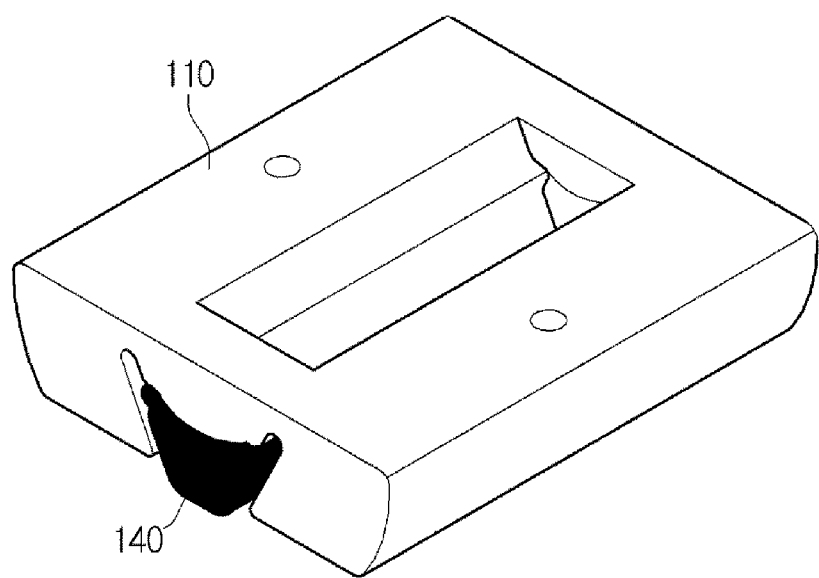
FIGS. 6A, 6B, and 6C illustrate a photoacoustic probe including a photoacoustic bracket covered with an inner cover, according to an exemplary embodiment of the present invention.
Figure 6B:
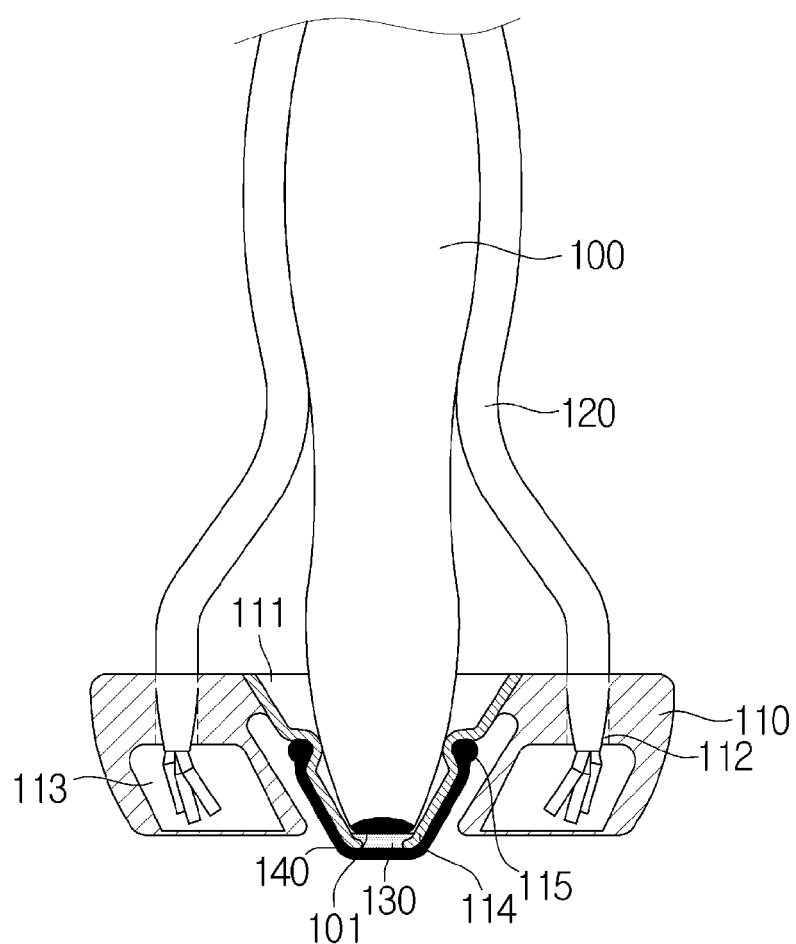
Figure 6C:
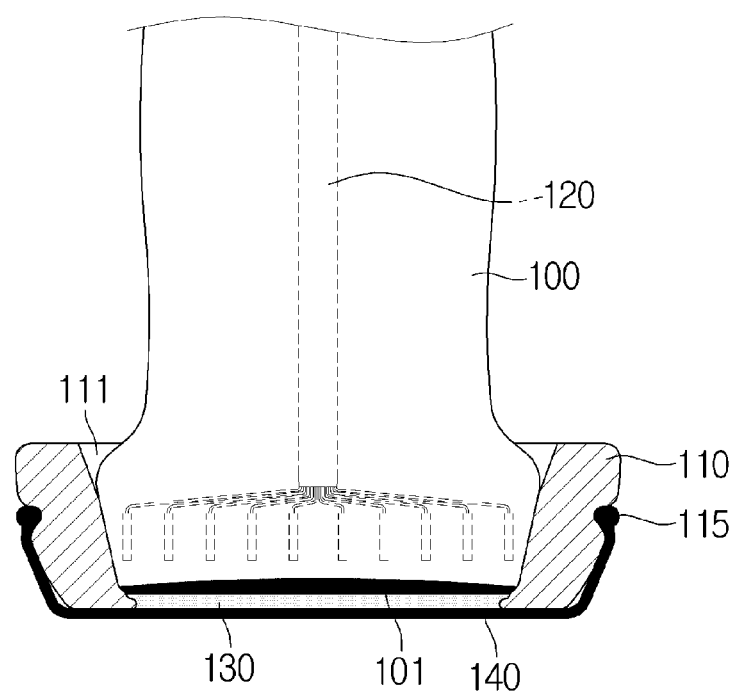

FIGS. 6A, 6B, and 6C illustrate the photoacoustic probe including the photoacoustic bracket 110 covered with an inner cover, according to an exemplary embodiment of the present invention, wherein FIG. 6A is a perspective view of the photoacoustic probe, FIG. 6B is a front sectional view of the photoacoustic probe, and FIG. 6C is a side sectional view of the photoacoustic probe.

Referring to FIGS. 6A, 6B, and 6C, an inner cover 140 may be configured to surround the space 114 in which the light reflector 130 is placed in the photoacoustic bracket 110. As described above, the inner cover 140 is used to prevent the light reflector 130 from leaking into the inner spaces 113 in which the ends of optical fibers are placed.

The inner cover 140 may include a circular loop for securely holding the inner cover 140 to the photoacoustic bracket 110. The circular loop is disposed along the groove 115 for holding the inner cover 140 so that the inner cover 140 is securely attached to the photoacoustic bracket 110 through the circular loop.

The inner cover 140 may be made of a material that is the same as or similar to that of a cover for a conventional ultrasonic probe. For example, the inner cover 140 may be made of polyurethane, latex, or polyethylene. Accordingly, the photoacoustic probe including the photoacoustic bracket 110 can perform diagnosis under the same conditions using the same method as the conventional ultrasonic probe.

Figure 7B:
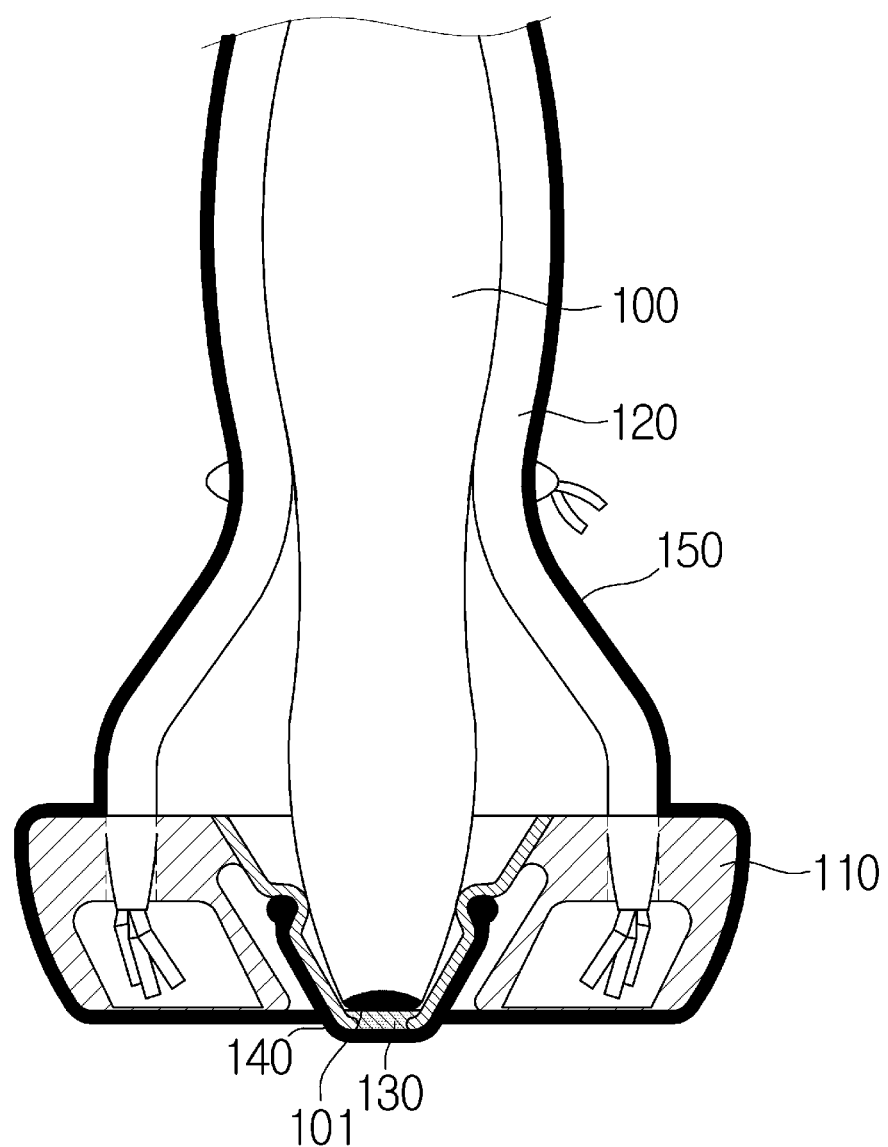
Figure 7C:
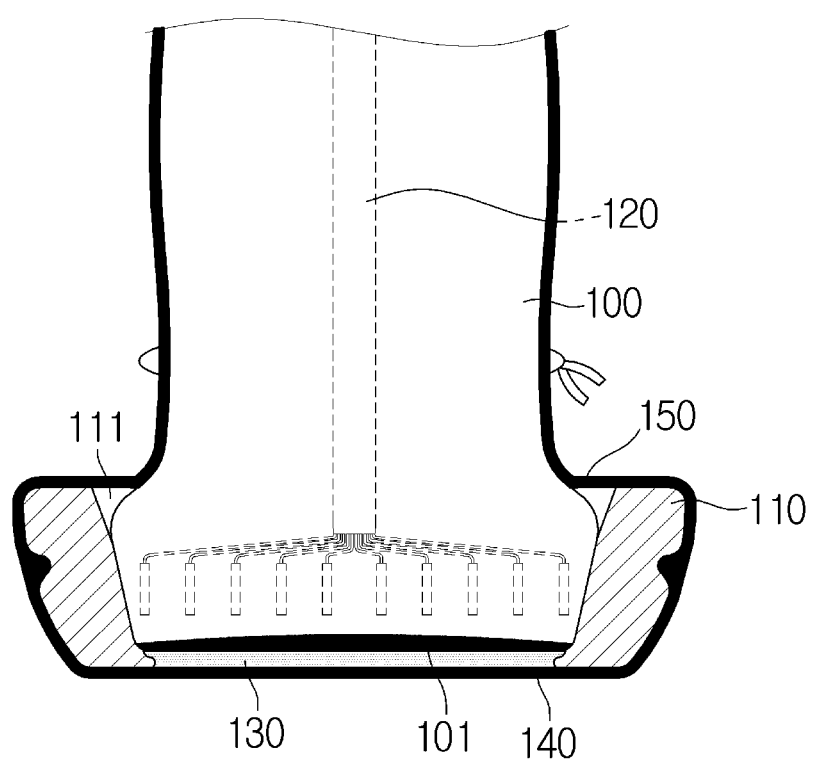

FIGS. 7A, 7B, and 7C illustrate the photoacoustic probe including the photoacoustic bracket covered with an inner cover and an outer cover, according to an exemplary embodiment of the present invention, wherein FIG. 7A is a perspective view of the photoacoustic probe, FIG. 7B is a front sectional view of the photoacoustic probe, and FIG. 7C is a side sectional view of the photoacoustic probe.

When a photoacoustic imaging apparatus is used in a general diagnosis room, a need to disinfect a photoacoustic probe or to cover the photoacoustic probe with a probe cover is relatively low. However, when a photoacoustic imaging apparatus is used in an operating room, there is a need to thoroughly manage and control the cleanliness of diagnostic equipment in order to avoid cross-contamination.

Accordingly, when a photoacoustic imaging apparatus is used in an operating room, a photoacoustic probe should be thoroughly sterilized and disinfected before it enters the operating room, and also used after being entirely covered with a probe cover.

For this purpose, an outer cover 150 to cover the photoacoustic probe is used. Referring to FIGS. 7A, 7B, and 7C, the outer cover 150 may wrap up the entire external surface of the photoacoustic probe, unlike the inner cover 140. Rubber bands may be used when wrapping up the photoacoustic probe with the outer cover 150 in order to securely hold the outer cover 150 on the photoacoustic probe while bringing it into close contact with the photoacoustic probe.

The outer cover 150 may be, like the inner cover 140, made of a rubber material that is the same as or similar to that of a cover for a conventional ultrasonic probe. For example, the outer cover 150 may be made of polyurethane, latex, or polyethylene. When the outer cover 150 is made of the same material as that of a cover for a conventional ultrasonic probe, conventional couplant for ultrasonic waves may be used as couplant for photoacoustic waves for impedance matching. That is, the outer cover 150 made of the same material as the conventional cover for ultrasonic waves enables compatibility with other equipment (material) for ultrasonic diagnosis.

When the inner cover 140 and the outer cover 150 are made of the same rubber material, the inner cover 140 and the outer cover 150 may constitute a single photoacoustic probe cover. That is, the inner cover 140 and the outer cover 150 may be produced as a single cover, or may be separately produced and then bonded later. When the inner cover 140 and the outer cover 150 are separately produced and then bonded, the inner cover 140 and the outer cover 150 may be bonded by Radio Frequency (RF) adhesion which is one of rubber adhesion processes. However, the inner cover 140 and the outer cover 150 may be bonded by any other rubber adhesion process.

Figure 8A:
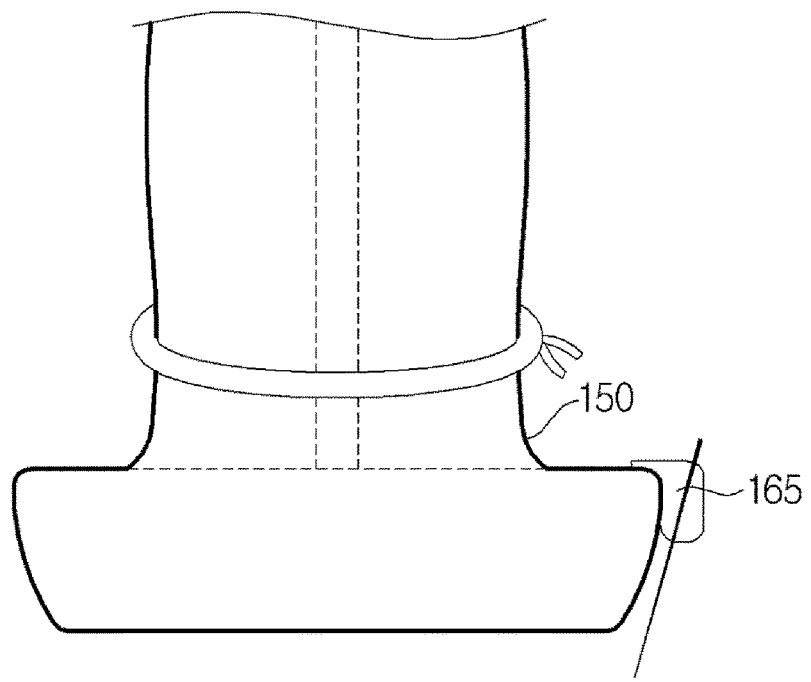
FIGS. 8A and 8B illustrate a photoacoustic probe including a biopsy needle kit, according to an exemplary embodiment of the present invention.
Figure 8B:
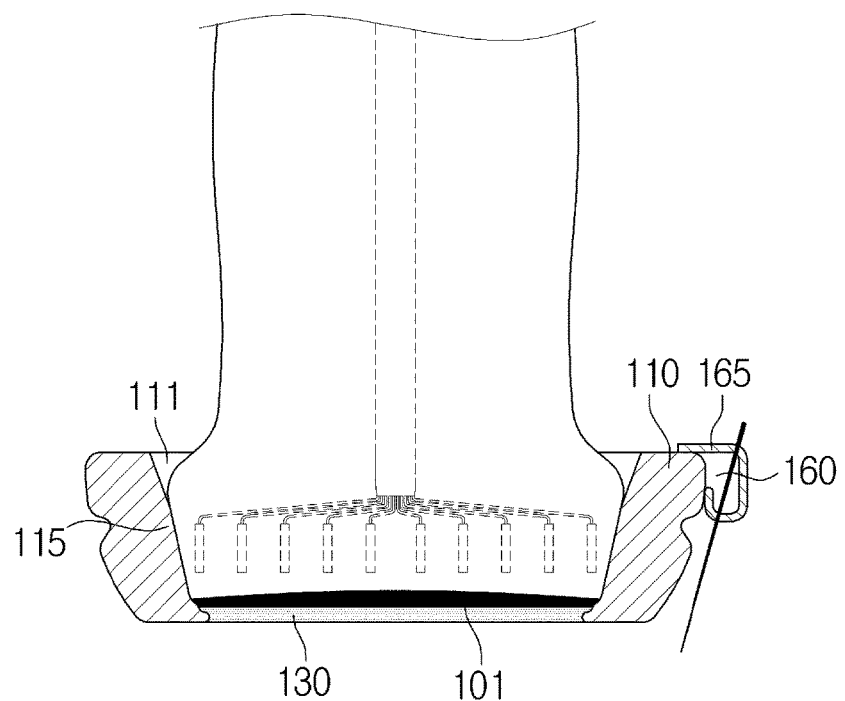

FIGS. 8A and 8B illustrate a photoacoustic probe including a biopsy needle kit, according to an exemplary embodiment of the present invention, wherein FIG. 8A is a side view of the photoacoustic probe, and FIG. 8B is a side sectional view of the photoacoustic probe.

When a tumor or a tissue suspected as a tumor was found in a body part of a patient, a biopsy which is cytological examination is generally taken. If the tumor is seen with naked eyes or checked with hands from outside, a biopsy can be easily taken by inserting a biopsy needle into the tumor region without having to use ultrasonic waves. However, when the tumor is not seen with naked eyes or cannot be checked with hands from outside, a biopsy using an ultrasonic diagnosis apparatus is taken.

In order to insert a biopsy needle into an exact lesion region when a biopsy is taken under the instruction of ultrasonic waves, a bracket enabling a biopsy needle kit to be coupled with an ultrasonic probe may be used. The bracket and the kit together guide the biopsy needle, thereby helping the biopsy needle be inserted into an exact lesion region, resulting in improvement of accuracy of biopsy.

Likewise, when a biopsy needle is coupled with a photoacoustic probe to take a biopsy, the same effect as described above can be also obtained. Referring to FIGS. 8A, and 8B, like a conventional biopsy bracket for ultrasonic waves, a biopsy needle kit coupler 160 for coupling with a biopsy needle kit 165 may be provided in one side of the photoacoustic bracket 110. The biopsy needle kit 165 is coupled with the biopsy kit coupler 160 of the photoacoustic bracket 110 to increase accuracy of diagnosis when photoacoustic diagnosis is performed together with a biopsy.

The biopsy needle kit coupler 160 may be configured for the biopsy needle kit 165 to be coupled with the biopsy kit needle coupler 160 in the same coupling method in which a biopsy needle kit is coupled with a conventional bracket for an ultrasonic probe. Accordingly, the biopsy needle kit coupler 160 can be compatible with a biopsy needle kit for ultrasonic diagnosis. However, the biopsy needle kit coupler 160 may be coupled with a photoacoustic biopsy needle kit 165 in consideration of structural conditions.

Figure 9B:
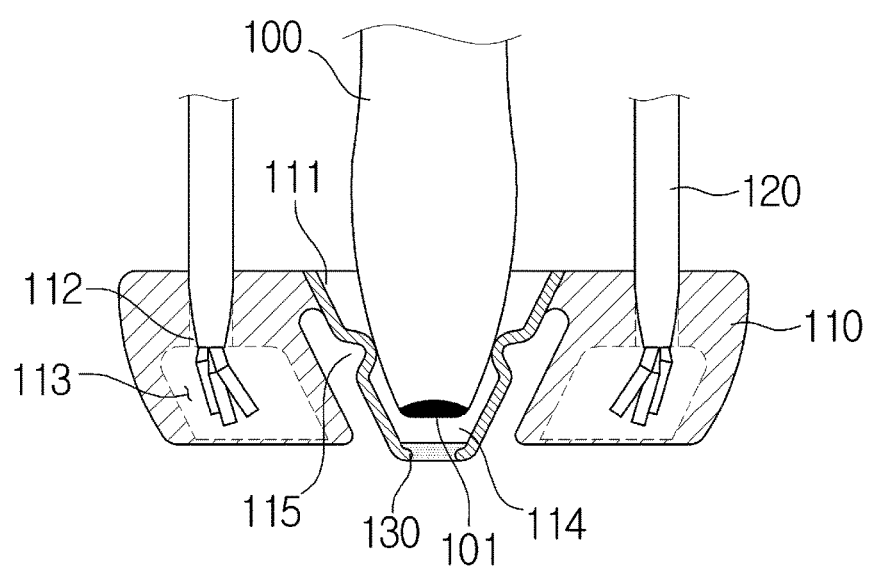
Figure 9C:
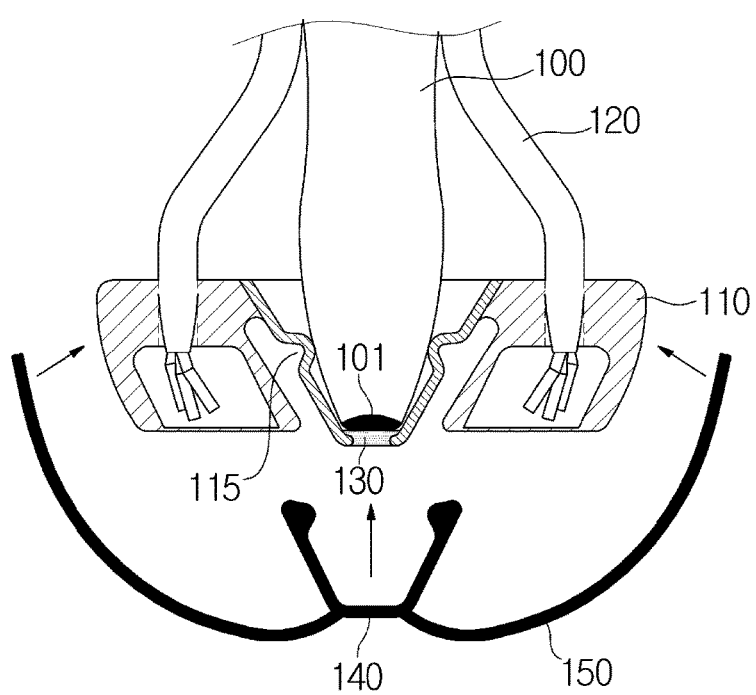

FIGS. 9A, 9B, and 9C illustrate an order in which a conventional ultrasonic probe is used as the photoacoustic probe.

FIG. 9A illustrates a step of inserting the ultrasonic probe 100 into the photoacoustic bracket 110. An ultrasonic probe 100 may be coupled with the probe coupling part 111 of the photoacoustic bracket 110. The ultrasonic probe 100 that is attached to the photoacoustic bracket 110 may be one of various kinds of conventional ultrasonic probes. The ultrasonic probe 100 may be coupled with the photoacoustic bracket 110 using a method such as interference fit or notch.

The optical fibers 120 may be inserted into the optical fiber inserting holes 112 of the photoacoustic bracket 110. FIG. 9A shows a case in which two bundles of optical fibers 120 are respectively inserted in the optical fiber inserting holes 112, however, the number of optical fibers 120 that are inserted in the photoacoustic bracket 110 is not limited so long as one or more optical fibers 120 are inserted in the photoacoustic bracket 110. The optical fibers 120 may be uniformly distributed over wide areas in the inner spaces 113 in which ends of the optical fibers 120 are placed, so that laser can be irradiated to a wide region of a target.

FIG. 9B illustrates a step of placing the fluid-type light reflector 130 into the photoacoustic bracket 110. The light reflector 130 may be placed into the space 114 formed below the acoustic lens 101 of the ultrasonic probe 100. When laser irradiated to a target returns to the photoacoustic probe due to scattering, the light reflector 130 again reflects the laser back toward the target to thus block the acoustic lens 101 from receiving the laser. Thereby, it is possible to reduce artifacts and increase accuracy of acoustic images.

FIG. 9C illustrates a step of covering the photoacoustic probe with the inner cover 140 and the outer cover 150. The inner cover 140 may surround the space 114 in which the light reflector 130 is placed. Thereby, the inner cover 140 can prevent the light reflector 130 from interfering with a transmission path of laser irradiated from the optical fibers 120. The photoacoustic bracket 110 may include a groove 115 for securely holding the inner cover 140, and a circular loop of the inner cover 140 may be coupled with the groove 115 to securely hold the inner cover 140 to the photoacoustic bracket 110.

The outer cover 150 may be used to wrap up the photoacoustic probe. By covering the photoacoustic probe with the outer cover 150 when the photoacoustic probe is used in an operating room with a higher risk of cross-contamination than in a general diagnosis room, the risk of cross-contamination can be minimized. Also, rubber bands to securely hold the outer cover 150 may be used.

The inner cover 140 and the outer cover 150 may be made of the same rubber material as a cover for a conventional ultrasonic probe. The inner cover 140 and the outer cover 150 made of a rubber material enable compatibility with other equipment (material) for ultrasonic diagnosis. Specifically, conventional couplant for ultrasonic waves may be used as couplant for the photoacoustic probe for impedance matching.

When the inner cover 140 and the outer cover 150 are made of the same rubber material, the inner cover 140 and the outer cover 150 may constitute a single photoacoustic probe cover. Alternatively, the inner cover 140 and the outer cover 150 may be separately produced and then bonded later using a rubber adhesion process, for example, RF adhesion.

The photoacoustic probe may be used for medical purposes, for example, diagnosis, treatment, operation, etc., targeting biologic tissues. However, the photoacoustic probe may be used in all behaviors targeting biologic tissues other than medical purposes. Furthermore, the photoacoustic probe may be used to examine non-biologic tissues when their photoacoustic images are needed.

Figure 10:
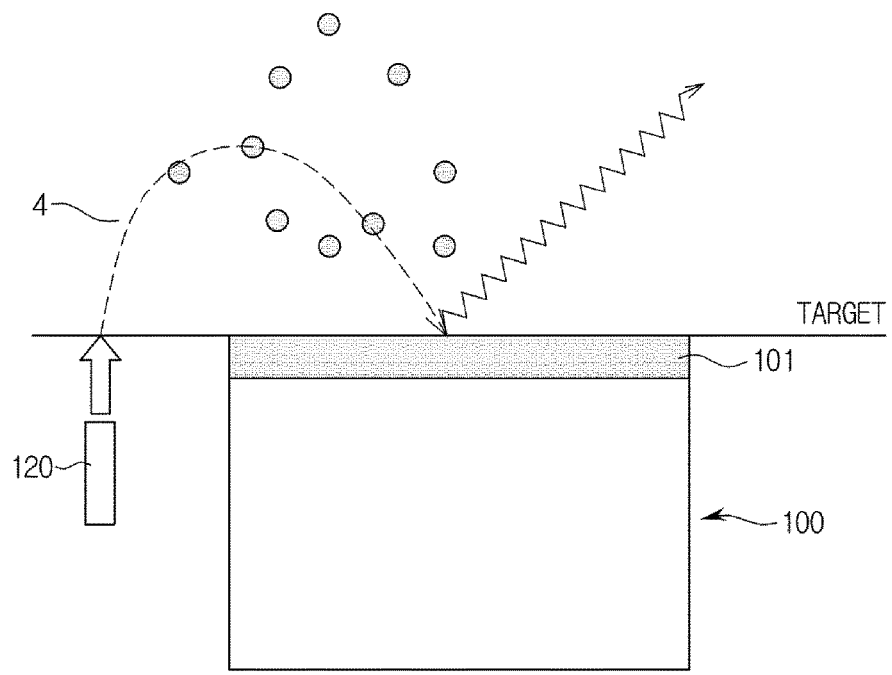
FIG. 10 is a view for describing an effect of a photoacoustic probe including a light reflector, according to an exemplary embodiment of the present invention.

FIG. 10 is a view for describing an effect of the photoacoustic probe including the light reflector 130, according to an exemplary embodiment of the present invention. Referring to FIG. 1, when a photoacoustic probe having no light reflector irradiates laser to a target, a part of the irradiated laser is scattered by light scatterers 3 in the target. The scattered laser may be absorbed by the acoustic lens 101, and the acoustic lens 101 generates acoustic waves by absorbing the laser. The acoustic waves are again radiated, thereby making artifacts.

Meanwhile, referring to FIG. 10, when a part of laser irradiated to a target is scattered by light scatterers 3 and then directed toward the acoustic lens 101, the light reflector again reflects the scattered laser toward the target. Accordingly, the acoustic lens 101 generates no acoustic waves, which are generated when the acoustic lens 101 absorbs the scattered laser, resulting in reduction of artifacts.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A photoacoustic probe comprising:
   at least one optical fiber irradiating laser to a target;
   an ultrasonic probe collecting a photoacoustic signal generated by the target having absorbed the laser;
   a photoacoustic bracket with which the ultrasonic probe and the optical fiber are coupled; and
   a fluid-type light reflector reflecting laser reflected, scattered, or retracted from the target,
   wherein the fluid-type light reflector serves to match an acoustic impedance,
   wherein the fluid-type light reflector is provided to flow,
   wherein the photoacoustic bracket includes a space spaced apart from the coupled the ultrasonic probe and formed in a collection path of the photoacoustic signal, and
   wherein the space is filled with the fluid-type light reflector to prevent the laser reflected, scattered, or refracted from the target from being collected by the ultrasound probe through the collection path of the photoacoustic signal.

2. The photoacoustic probe according to claim 1, wherein a laser generator is connected to one end of the optical fiber.

3. The photoacoustic probe according to claim 2, wherein when a plurality of optical fibers are provided, the plurality of optical fibers are connected in series or in parallel to the laser generator.

4. The photoacoustic probe according to claim 1, wherein the laser is single-wavelength laser or multi-wavelength laser.

5. The photoacoustic probe according to claim 1, wherein the laser is pulsed laser or continuous laser.

6. The photoacoustic probe according to claim 1, wherein the ultrasonic probe is a linear probe, a convex probe, or a phased array probe.

7. The photoacoustic probe according to claim 1, wherein the fluid-type light reflector contains zinc oxide (ZnO) or titanium oxide (TiO).

8. The photoacoustic probe according to claim 1, comprising an inner cover blocking the light reflector from leaking out.

9. The photoacoustic probe according to claim 8, comprising an outer cover covering the outer surface of the photoacoustic probe in order to avoid cross-contamination of the target.

10. The photoacoustic probe according to claim 9, wherein the inner cover and the outer cover are made of a rubber material that transmits both ultrasonic waves and laser.

11. The photoacoustic probe according to claim 10, wherein the inner cover and the outer cover are connected to each other by a Radio Frequency (RF) adhesion process.

12. The photoacoustic probe according to claim 1, wherein the photoacoustic bracket is coupled with a biopsy needle kit.

13. The photoacoustic probe according to claim 1, wherein the target includes a biologic tissue and a non-biologic tissue.

14. A photoacoustic imaging apparatus comprising:
a photoacoustic probe irradiating laser to a target and collecting a photoacoustic signal; and
a main body converting the collected photoacoustic signal into an image signal,
wherein the photoacoustic probe comprises:
at least one optical fiber irradiating laser to a target;
an ultrasonic probe collecting a photoacoustic signal which is generated by the target having absorbed the laser;
a photoacoustic bracket with which the ultrasonic probe and the optical fiber are coupled; and
a fluid-type light reflector reflecting laser reflected, scattered, or refracted from the target,
wherein the fluid-type light reflector serves to match an acoustic impedance, and
wherein the fluid-type light reflector is provided to flow,
wherein the photoacoustic bracket includes a space which is spaced apart from the coupled the ultrasonic probe and is formed in a collection path of the photoacoustic signal, and
wherein the space is filled with the fluid-type light reflector to prevent the laser reflected, scattered, or refracted from the target from being collected by the ultrasound probe through the collection path of the photoacoustic signal.

15. The photoacoustic imaging apparatus according to claim 14, wherein the photoacoustic probe comprises an inner cover blocking the light reflector placed in the photoacoustic bracket from leaking out.

16. The photoacoustic imaging apparatus according to claim 15, wherein the photoacoustic probe comprises an outer cover covering the outer surface of the photoacoustic probe in order to avoid cross-contamination of the target.

17. A photoacoustic bracket comprising:
a probe coupling part with which an ultrasonic probe is coupled;
an optical fiber coupling part with which an optical fiber is coupled; and
a space, which is spaced apart from the probe coupling part and is formed in a collection path of a photoacoustic signal by the ultrasonic probe,
wherein the fluid-type light reflector serves to match an acoustic impedance,
wherein the fluid-type light reflector is provided to flow, and
wherein the space is filled with the fluid-type light reflector to prevent laser reflected, scattered, or refracted from a target from being collected by the ultrasound probe through the collection path of the photoacoustic signal.

18. The photoacoustic bracket according to claim 17, wherein the optical fiber coupling part comprises:
an optical fiber inserting hole in which the optical fiber is inserted; and
an inner space in which an end of the optical fiber is placed.

19. The photoacoustic bracket according to claim 17, comprising a groove holding an inner cover for blocking the light reflector from leaking out.

20. The photoacoustic bracket according to claim 17, comprising a biopsy needle kit coupler that is coupled with a photoacoustic biopsy needle kit.

\* \* \* \* \*